US012590277B2

(12) United States Patent
Guo

(10) Patent No.: US 12,590,277 B2
(45) Date of Patent: Mar. 31, 2026

(54) HIGH-THROUGHPUT ACOUSTOFLUIDIC FABRICATION OF CELL SPHEROIDS

(71) Applicant: The Trustees of Indiana University, Bloomington, IN (US)

(72) Inventor: Feng Guo, Bloomington, IN (US)

(73) Assignee: The Trustees of Indiana University, Bloomington, IN (US)

( * ) Notice: Subject to any disclaimer, the term of this patent is extended or adjusted under 35 U.S.C. 154(b) by 1224 days.

(21) Appl. No.: 17/598,097

(22) PCT Filed: Mar. 26, 2020

(86) PCT No.: PCT/US2020/024927
§ 371 (c)(1),
(2) Date: Sep. 24, 2021

(87) PCT Pub. No.: WO2020/198455
PCT Pub. Date: Oct. 1, 2020

(65) Prior Publication Data
US 2022/0106548 A1      Apr. 7, 2022

Related U.S. Application Data

(60) Provisional application No. 62/908,646, filed on Oct. 1, 2019, provisional application No. 62/823,776, filed on Mar. 26, 2019.

(51) Int. Cl.
| *C12M 3/06* | (2006.01) |
| *C12M 1/42* | (2006.01) |
| *C12N 5/09* | (2010.01) |

(52) U.S. Cl.
CPC ............ *C12M 23/16* (2013.01); *C12M 35/04* (2013.01); *C12N 5/0693* (2013.01); *C12N 2527/00* (2013.01)

(58) Field of Classification Search
CPC ...................................................... C12M 23/16
See application file for complete search history.

(56) References Cited

U.S. PATENT DOCUMENTS

| 5,539,362 A | 7/1996 | Culling |
| 2018/0038449 A1 | 2/2018 | Barger |
| 2018/0038499 A1 | 2/2018 | Juncker et al. |

FOREIGN PATENT DOCUMENTS

| DE | 102010052197 A1 * | 5/2012 | ............ C12M 23/12 |
| KR | 20130103653 A * | 9/2013 | |

(Continued)

OTHER PUBLICATIONS

Chen et al., "High-throughput acoustofluidic fabrication of tumor spheroids", Mar. 25, 2019, Royal Society of Chemistry, vol. 19 , pp. 1755-1763 (Year: 2019).*

(Continued)

*Primary Examiner* — Elizabeth A Robinson
*Assistant Examiner* — Jonathan E Lepage
(74) *Attorney, Agent, or Firm* — Faegre Drinker Biddle & Reath LLP

(57) ABSTRACT

Disclosed is an apparatus, such as an acoustofluidic device, for high-throughput fabrication of multicellular spheroids. The device has a chamber substrate having at least one cell assembly channel; an acoustic transducer; and, a coupling layer disposed between the chamber substrate and the acoustic transducer.

7 Claims, 15 Drawing Sheets

(56)  References Cited

FOREIGN PATENT DOCUMENTS

| WO | WO-2012027366 A2 * | 3/2012 | ........ B01L 3/502761 |
| WO | WO-2015134831 A1 * | 9/2015 | ........... G01N 29/022 |

OTHER PUBLICATIONS

Chen, Bin et al., "High-Throughput Acoustofluidic Fabrication of TumorSperoids," Lab Chip, Mar. 25, 2019, vol. 19, No. 10, 20 pgs.
International Search Report and Written Opinion, issued by the ISA/US, Commissioner for Patents, dated Aug. 7, 2020, for International Application No. PCT/US2020/024927; 13 pages.

* cited by examiner

After Standing Wave

Before Standing Wave

— Proliferating Zone
— Quiescent Zone
— Necrotic Zone

Table 1. Cell spheroid formation methods

| Technique | Time required [Day] | Cell Number required [×10⁶] | Number of spheroids | Uniformity Control |
|---|---|---|---|---|
| OPTOAcoustic Device | 1 | 0.2 | High (>6,000) | Yes |
| Spheroid microplate | 3-7 | 0.5 | Low (96-384) | No |
| Hanging drop | 7 | 0.5 | Low (96-384) | Yes |
| Magnetic levitation | 7 | 0.5 | Low (96) | Yes |
| Spinner-flask | 14-35 | 5 | High | No |

FIG. 8

HIGH-THROUGHPUT ACOUSTOFLUIDIC FABRICATION OF CELL SPHEROIDS

CROSS-REFERENCE TO RELATED APPLICATION

This application is a national phase filing of International Application No. PCT/US2020/024927, filed Mar. 26, 2020, which claims the benefit of U.S. Provisional Application Ser. No. 62/908,646, filed Oct. 1, 2019, entitled HIGH-THROUGHPUT ACOUSTOFLUIDIC FABRICATION OF TUMOR SPHEROIDS and also claims the benefit of U.S. Provisional Application Ser. No. 62/823,776, filed Mar. 26, 2019, entitled HIGH-THROUGHPUT ACOUSTOFLU-IDIC FABRICATION OF TUMOR SPHEROIDS. The above mentioned applications are hereby incorporated by reference in their entireties.

FIELD OF THE DISCLOSURE

The devices and methods described herein generally relate to a device, such as an acoustofluidic device, for producing multicellular spheroids from individual cells at a high rate, particularly an acoustofluidic device that produces standing surface acoustic waves to force the clustering of individual cells into multicellular clusters that during incubation develop into multicellular spheroid-like clusters, which are then transferred to a dish for final culturing into multicellular spheroids.

BACKGROUND

Drug screening typically requires the use of numerous cells. Traditional in vitro drug screening has historically been based on creating two-dimensional (2D) cell cultures (i.e., cell monolayers) on plastic surfaces. However, the 2D cell cultures often cannot recreate or mimic the in vivo physiological conditions, such as the complex microenvironment, due to the lack of appropriate cell-cell and cell-matrix interactions and the absence of tissue-specific architecture, such as the mechanical, and chemical cues that are essential for unique functions of tissues and organs in the body. The absence of physical-biochemical characteristics of a cell monolayer generally leads to increased efficiency of drugs targeting specific molecular targets; in the long-term, however, this absence contributes to the high failure rate of compounds at the later stages of drug development.

In an attempt to overcome this limitation, three-dimensional (3D) cell culture methods have been developed to better represent the in vivo microenvironment and mimic the physiological functions of living tissues when investigating the response to therapeutic agents. Spheroid formation is recognized in the art as a well characterized model for 3D culture and screening due to its simplicity, reproducibility, and similarity to physiological tissues as compared to 2D cell cultures and other scaffold-based methods. Spheroids are self-assembled spherical clusters of cell colonies cultured in environments where cell-cell interactions dominate over cell-substrate interactions, and the spheroids more naturally mimic avascular tumors with inherent metabolic (oxygen) and proliferative (nutrient) gradients. As such, 3D tumor spheroids offer a desirable biomimetic microenvironment that is appropriate for recapitulating tissue cellular adhesive complexity and revealing a more realistic drug response. 3D tumor spheroid culture is considered as an improved in vitro model to mimic biological properties of poorly vascularized regions of tumors and non-vascularized micro-metastases because spheroids retain the architecture and many morphological and physiological characteristics of their tumor counterparts.

Although tumor spheroids have been widely recognized and served as excellent physiologic tumor models, it has been difficult to scale up spheroid culture for screening and testing. Traditional 3D spheroid formation and culture systems and methods include liquid overlay methods, hanging drop methods, non-adherent surfaces, agitation based approaches and devices such as spinner flask cultures, scaffold structures, and micro/nanostructures. However, these systems and methods typically require complex set-up, are time consuming, yield low throughput, and often produce spheres of irregular size leading to many difficulties in scaling up.

Recently, patterned surfaces and various microfluidic devices have been developed to increase spheroid formation efficiency and simplify handling procedures. Potentially significant advantages of microfluidic devices include providing controlled mixing, chemical concentration gradients, lower reagent consumption, continuous perfusion, and precision control of shear stress on cells. Many of these techniques, nonetheless, still suffer from problems such as the inability to support long-term culture and incompatibility with high-throughput drug screening.

SUMMARY

What is needed is a device and method of producing and fabricating multicellular spheroids at a high rate. This disclosure describes a device and method of satisfying that need by utilizing acoustofluidics, which is the combination of acoustics and microfluidics, to efficiently create a scalable model for producing and fabricating multicellular spheroids at a high rate. Particularly, acoustofluidics, which includes the application of a surface acoustic wave that is used to cluster individual cells during incubation of the individual cells to develop three-dimensional multicellular clusters from which 3D multicellular spheroid-like structures can develop, and which are then transferred to, for instance, a dish for further culturing into 3D multicellular spheroids, thereby providing an improved approach to multicellular spheroid fabrication because first creating multi-cell clusters and spheroid-like structures in this manner significantly reduces the overall time to produce multicellular 3D spheroids. Such an approach provides the benefits of excellent biocompatibility, flexibility, and contactless and label-free manipulation of cells while preserving the cells' native state. In comparison with conventional 3D spheroid formation methods, the device and method of the present disclosure provide a platform that has several advantages including: (i) high generation yield and reproducibility of multicellular spheroids, (ii) fast multicellular spheroid assembly with controllable size, (iii) long term culture that maintains high viability, (iv) applicability to a wide range of cells lines, and (v) high-throughput drug screening with close-to-physiological medium flow conditions.

A device of the present disclosure for fabricating multicellular spheroids from individual cells comprises: an interdigital transducer having a first end, a second end, a length between the first end and the second end, and a longitudinal axis parallel to the length, wherein the interdigital transducer is configured to produce a plurality of surface waves substantially parallel to the length; a substrate having an array of channels, wherein each of the channels has a first end, a second end, a length between the first end and the second end, and a longitudinal axis parallel to the length, wherein the substrate is disposed over the interdigital transducer and oriented such that the longitudinal axis of the channels is parallel with the longitudinal axis of the interdigital transducer; and a signal generator coupled to the interdigital transducer, wherein the generator produces an alternating signal to the interdigital transducer at a frequency between 0.5 megahertz and 50 megahertz and the interdigital transducer creates surface waves within suspension liquid contained within the channels, wherein the suspension liquid comprises a plurality of individual cells, and wherein the surface waves produce a plurality of pressure nodes within the channels and the surface waves move the individual cells toward the pressure nodes, thereby facilitating the formation of multicellular clusters at the pressure nodes.

The device of the previous paragraph, further comprising a fluid layer disposed between the array and the interdigital transducer.

The device of any of the previous paragraphs, wherein the fluid layer comprises mineral oil.

The device of any of the previous paragraphs, further comprising a means for coupling the substrate to the interdigital transducer.

The device of any of the previous paragraphs, wherein the means for coupling the substrate to the interdigital transducer comprises a peg and hole arrangement.

The device of any of the previous paragraphs, wherein the substrate further comprises a first plurality of recesses disposed at the first end of the channels and a second plurality of recesses disposed at the second end of the channels, wherein one of the first plurality of recesses is greater in size than another of the first plurality of recesses, wherein the one of the first plurality of recesses is further from the first end of the channel and is in fluid communication with the other of the first plurality of recesses.

The device of any of the previous paragraphs, wherein the substrate further comprises a second plurality of recesses disposed at the second end of the channels, wherein one of the second plurality of recesses is greater in size than another of the second plurality of recesses, wherein the one of the second plurality of recesses is further from the second end of the channel and is in fluid communication with the other of the first plurality of recesses.

A method of the present disclosure for fabricating multicellular clusters comprises: providing an optoacoustic device comprising: an acoustic interdigital transducer having a first end, a second end, a length between the first end and the second end, and a longitudinal axis parallel to the length, wherein the interdigital transducer configured to produce a plurality of surface waves substantially parallel to the length; a substrate having an array of channels, wherein each of the channels has a first end, a second end, a length between the first end and the second end, and a longitudinal axis parallel to the length; randomly inserting a suspension fluid comprising a plurality of individual cells into the channels; during an incubation phase for the plurality of cells, applying an alternating signal to the transducer at a frequency between 0.5 megahertz and 50 megahertz, thereby creating surface waves within the suspension liquid contained within the channels, wherein the surface waves produce a plurality of pressure nodes within the channels and the surface waves move the individual cells toward the pressure nodes, thereby facilitating the formation of multicellular clusters at the pressure nodes in an array pattern within the channels.

The method of the previous paragraph, wherein the substrate is disposed over the interdigital transducer and oriented such that the longitudinal axis of the channels is parallel with the longitudinal axis of the interdigital transducer.

The method of any of the previous paragraphs, further comprising incubating the multicellular clusters into multicellular spheroid-likes structures.

The method of any of the previous paragraphs, further comprising: washing the multicellular clusters or multicellular spheroid-like structures from at least one channel in the array; and, transferring the multicellular clusters or multicellular spheroid-like structures to a dish.

The method of any of the previous paragraphs, further comprising culturing the multicellular clusters or the multicellular structures in the dish and forming multicellular spheroids.

A device of the present disclosure for fabricating multicellular spheroids from individual cells, the device comprises: a means for producing a plurality of parallel surface acoustic waves substantially parallel to the length, wherein the surface acoustic waves comprise a frequency between 0.5 megahertz and 50 megahertz; a substrate having an array of channels, wherein each of the channels has a first end, a second end, a length between the first end and the second end, and a longitudinal axis parallel to the length, wherein the substrate is disposed over the means for producing a plurality of parallel surface acoustic waves and oriented such that the longitudinal axis of the channels is parallel with parallel surface acoustic waves; and wherein the surface acoustic waves produce a plurality of pressure nodes within the channels and the surface acoustic waves move the individual cells toward the pressure nodes, thereby facilitating the formation of multicellular clusters in an array pattern within the channels.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 8 is a comparison of the results of different multicellular spheroid formation methods.

It should be understood that the drawings and replicas of the photographs are not necessarily to scale. In certain instances, details that are not necessary for an understanding of the disclosure or that render other details difficult to perceive may have been omitted. It should be understood, of course, that the disclosure is not necessarily limited to the particular examples or embodiments illustrated or depicted herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1A:
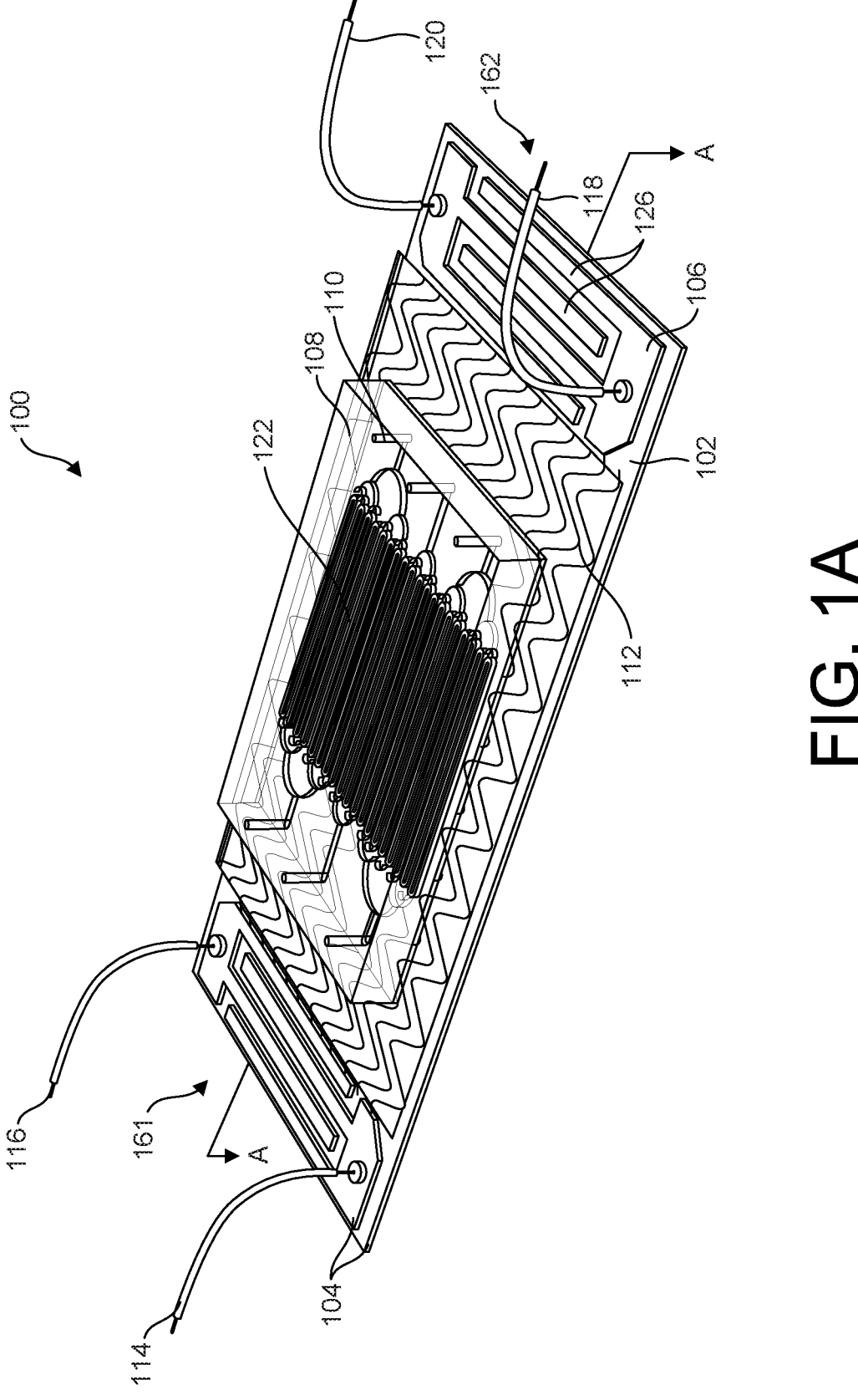
FIG. 1A illustrates a perspective view of an example of an acoustofluidic device for creating multicellular clusters according to the present disclosure.
Figures 1B, 1C:
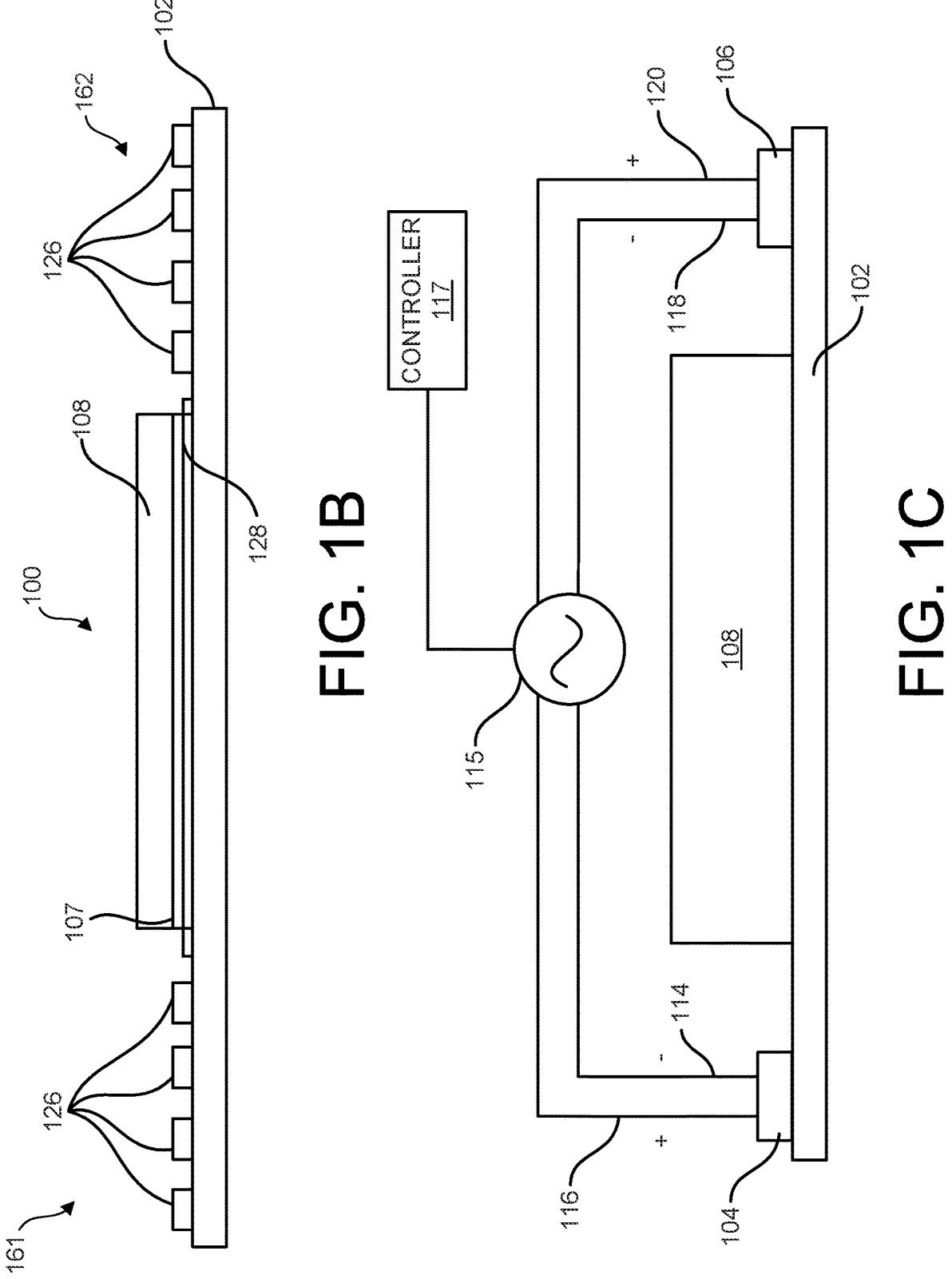
FIG. 1B illustrates a cross-section of the acoustofluidic device depicted in FIG. 1A.
FIG. 1C illustrates a schematic view of the acoustofluidic device depicted in FIG. 1A along with a signal generator and a controller.

Referring to a FIG. 1A, there is depicted a perspective view of an example of an acoustofluidic device 100 for creating uniformly-shaped multicellular cell clusters from individual cells from which multicellular spheroid-like structures and multicellular spheroids may be developed at a high rate. The acoustofluidic device 100 includes a means for producing a plurality of parallel standing surface acoustic waves, such as a standing surface acoustic wave generator, and a chamber 108 having an array 122 of channels 124 disposed over the means for producing a plurality of parallel surface acoustic waves. One example of a standing surface acoustic wave generator is an interdigital transducer (IDT), which is a device that comprises two electrodes 104, 106 deposited on opposite ends of a surface of a piezoelectric substrate 102, such as quartz or lithium niobite. Referring to FIGS. 1A and 1B, one electrode 104 is disposed on the left side 161 of the piezoelectric substrate 102 and another electrode 106 is disposed on the right side 162 of the piezoelectric substrate 102, wherein the electrodes 104, 106 are separated by a length.

Each electrode 104, 106 may be constructed of photoresist material and formed by an interlocking comb-shaped array that includes a plurality of separated fingers 126. When a radio frequency (RF) or an alternating current (AC) signal is applied to the electrodes, the piezoelectric substrate 102 vibrates at the frequency of the RF signal. The vibration creates standing surface acoustic wave (SAW) on the surface of the piezoelectric substrate 102. A SAW also propagates along fluid disposed over the surface of the piezoelectric substrate 102. As such, it may be desirable, to interpose a liquid layer 128, comprised of water or oil (e.g., mineral oil, olive oil, etc.), between the piezoelectric substrate 102 and the chamber 108. As will be discussed in more detail below, the chamber 108 comprises a plurality of channels 124, and it may be desirable for the channels 124 to extend as deep as possible into the bottom of the chamber 108. Hence, it may desirable for the channels 124 to extend all the way through the chamber 108 and apply a thin film 107 of the same or similar material as the chamber. If so, the film 107 is interposed between the liquid layer 128 and the chamber. Such a configuration may enhance the transfer of the SAWs into the channels 124.

The shape of SAWs, such as the resulting frequency, amplitude, and wave-front orientation of the acoustic waves, is at least partially dependent upon the pattern and dimensions of the electrodes, the RF signal (e.g., power of the signal), and the piezoelectric material, including the speed of sound in the material. For example, the frequency of the SAWs is defined by $v/\lambda$, where v is the speed of sound in the piezoelectric material and $\lambda$ is the acoustic wavelength. The wavelength ($\lambda$) of SAW is dependent on the width of the fingers 126 of the electrodes, as well as the spacing between fingers. It may be desirable to adjust the frequency or wavelength of the SAW. As such, referring to FIG. 1C, it may desirable for the acoustofluidic device 100 to include a signal generator 115, which produces the RF or AC signal, to be electrically coupled to a controller 117 that has the ability to alter the amplitude, frequency and/or wavelength of the RF or AC signal. The controller 117 may be generally representative of any device suitable for performing the processing and analysis techniques discussed within the present disclosure. In some examples, the controller 117 preferably includes a computer system comprising one or more processors and memory for storing programs and applications to perform the methods disclosed herein. Accordingly, it is understood that any steps related to data acquisition, data processing, instrument control, and/or other processing or control aspects of the present disclosure may be implemented by the computing systems using corresponding instructions stored on or in a non-transitory computer readable medium accessible by the computing device.

Figures 1D, 1E:
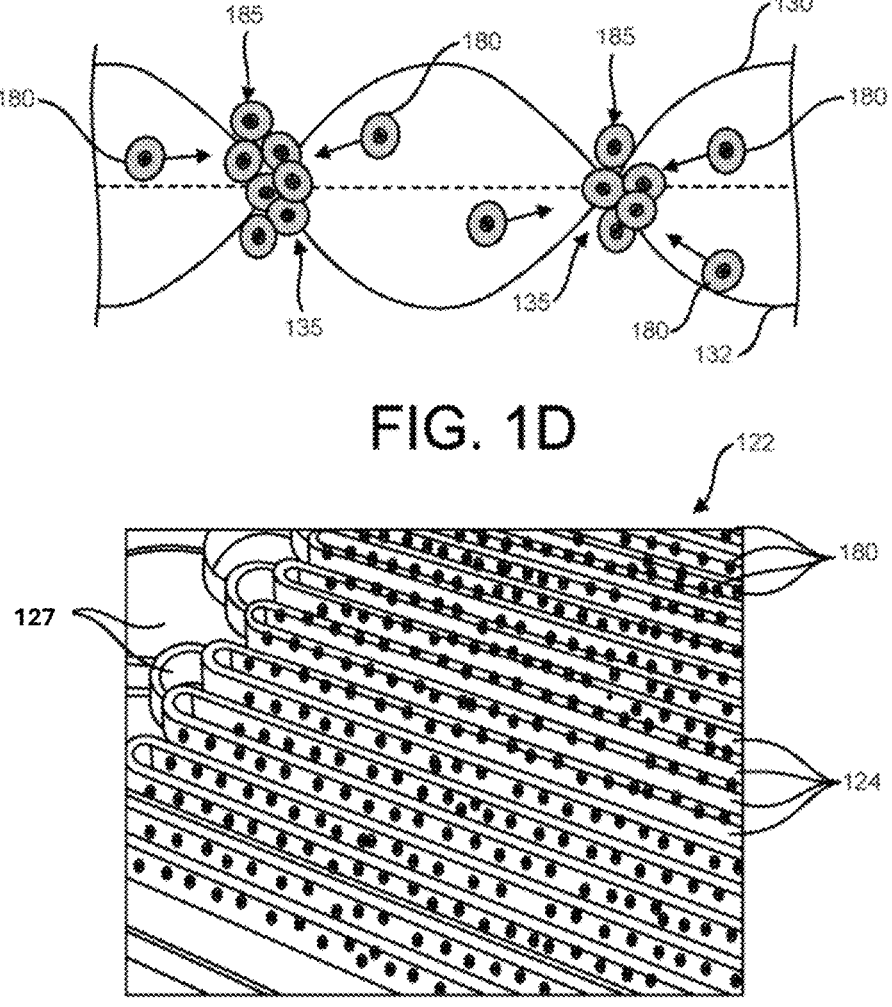
FIG. 1D illustrates a depiction of an example of an acoustic surface wave created by the acoustofluidic device depicted in FIG. 1A.
FIG. 1E illustrates a perspective view of a substrate having a plurality of channels incorporated in the acoustofluidic device of FIG. 1A and a plurality of single cells randomly placed within each of the channels, wherein the acoustofluidic device is in the OFF position.

Referring to FIGS. 1A and 1B, upon electrode 104 receiving an RF signal via electrical wires 114, 116, the electrode 104 creates a transverse wave that propagates from the left side 161 of the acoustofluidic device 100 to the right side 162 of the acoustofluidic device 100. Upon electrode 106 receiving an RF signal via electrical wires 118, 120, the electrode 106 creates a transverse wave that propagates from the right side 162 of the acoustofluidic device 100 to the left side 161 of the acoustofluidic device 100. Referring to FIG. 1D, one transverse wave is shown as item 130, and another transverse wave is shown as item 132. The transverse waves 130, 132 intersect and create a SAW depicted as item 134. The points at which the SAW intersects the imaginary axis are referred to as pressure nodes 135. Referring again to FIG. 1A, item 112 is a depiction of the acoustic field comprising a plurality of SAW extending between the left side 161 (electrode 104) and the right side 162 (electrode 106) of the acoustofluidic device 100. As such, the interdigital transducer is configured to produce a plurality of SAW substantially parallel to the length of the piezoelectric substrate 102 between the two electrodes 104, 106.

Referring to FIGS. 1A, 1B, 1E and 1F, another chamber 108 has an array 122 of channels 124. The chamber 108 may be constructed of polydimethylsiloxane (PDMS) or some other plastic. Each of the channels 124 has a first end, a second end, a length between the first end and the second end, and a pair of walls parallel with the length of each channel. That is, the walls of the channels 124 form a longitudinal structure that contain the individual cells 180 in close proximity to one another while the SAW(s) is/are applied, thereby ensuring that a sufficient quantity of pressure nodes 135 are formed within each channel 124. Each of the channels also has longitudinal axis that is parallel to the length of the channels. The chamber 108 is disposed over the interdigital transducer and the piezoelectric substrate 102 and oriented such that the longitudinal axis of the channels 124 is parallel with the longitudinal axis of the interdigital transducer and the length of the piezoelectric substrate 102 between the electrodes 104, 106. That is, each end of the channels 124 extend in a direction toward the electrodes 104, 106. It is preferable for the substrate 102 and channels 124 to be oriented in this manner so that multiple nodes 135 of the SAWs are created and exist in each channel 124. At the bottom of the chamber 108 and channels 124 is a thin film 107 is adhered to the chamber 108. The film 107 may be constructed of the same material as the chamber 108 or a different material. An example of the film 107 is a 25 micron (μm) thick PDMS.

The acoustofluidic device 100 also includes a means for coupling the chamber 108 to the interdigital transducer, thereby ensuring that the chamber 108 remains stationary while the SAWs are created. One such means may include a plurality of pegs extending from the piezoelectric substrate 102 and a corresponding number of holes in the chamber 108 to receive the pegs. Alternatively, the pegs may extend from the chamber 108 and the holes may exist in the piezoelectric substrate 102. Again, the IDT includes a piezoelectric substrate 102 above which a liquid layer 128 lays, and the chamber 108 has an array 122 of a plurality of channels 124 below which the thin film 107 is adhered to the chamber 108. The means for coupling the chamber 108 to the interdigital transducer also assists in aligning the channels 124 and the electrodes 104, 106 such that the SAWs 134 propagate within the channels 124 and multiple nodes 135 are formed in each channel.

Referring to FIG. 1E, there is depicted chamber 108 having an array 122 of a plurality of parallel channels 124. This figure also depicts a plurality of single cells 180 randomly placed within each of the channels 124. The cells 180 are disposed within a suspension liquid within each channel 124. The random nature of the cells 180 within the channels 124 is a result of the signal generator 115 being in the OFF position, thereby preventing the formation of SAWs and nodes 135 within the channels 124.

Figure 1F:
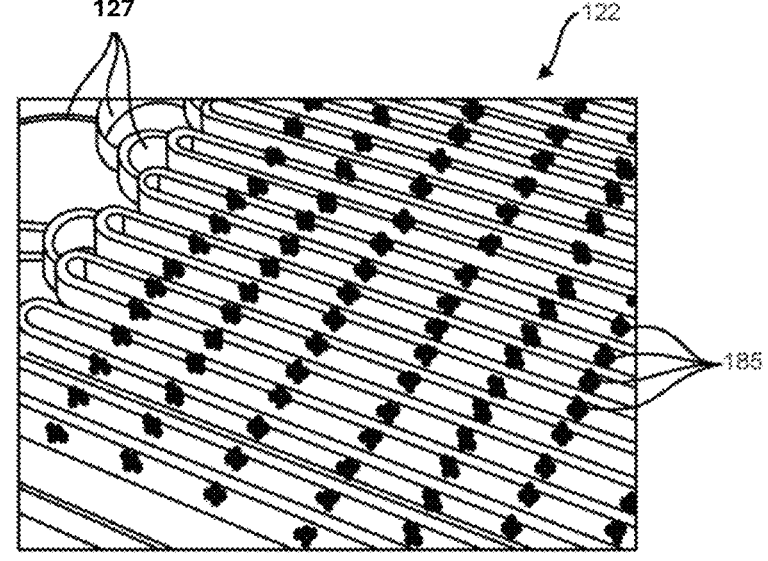
FIG. 1F illustrates a perspective view of a substrate having a plurality of channels incorporated in the acoustofluidic device of FIG. 1A, and a plurality of multicellular clusters arranged in array within each of the channels, wherein the acoustofluidic device is in the ON position.

Referring to FIG. 1F, there is depicted the same chamber 108 having an array 122 of a plurality of parallel channels 124 as shown in FIG. 1E. But rather than depicting a plurality of single cells 180 randomly placed within each of the channels 124, FIG. 1F depicts a plurality of generally evenly spaced multicellular clusters 185 within each channel 124. The multicellular clusters 185 are disposed within a suspension liquid within each channel 124. As shown in this FIGS. 1D and 1F, multicellular clusters 185 are aligned with the nodes 135 of the SAW 134. Upon the signal generator 115 being in the ON position, SAWs 134 and pressure nodes 135 within the channels 124 are created. The SAWs 134 push or move the single cells 180 toward the pressure nodes 135, thereby trapping the single cells 180 at the pressure nodes 135 and facilitating the formation of multicellular clusters 185 at the pressure nodes 135. That is, numerous multicellular clusters 185 can be formed simultaneously, from each of which multicellular spheroid-like structures and multicellular spheroids can be formed.

For example, assuming the chamber 108 comprises an array 122 of sixty (60) parallel channels 124, and each channel 124 has a length of 3 centimeter, a height of 150 microns and a width of 150 microns, about 12,000 pressure nodes could be formed at about the same time within chamber 108 and channels 124 using a plurality of SAWs 134 having wavelength of 300 μm and an RF signal having a frequency between 0.5 megahertz and 50 megahertz using the acoustofluidic device 100 of the present disclosure. Hence, within only minutes, rather than hours or days, thousands of uniformly-shaped multicellular clusters 185 can be produced, from each of which multicellular spheroid-like structures and multicellular spheroids can be formed. The acoustofluidic device 100 of the present disclosure has the advantage forming uniformly-shaped multicellular clusters 185 at a relatively high throughput rate in a short time. Additionally, the acoustofluidic device 100 and method of using the device is easy to operate. In short, the acoustofluidic device 100 of the present disclosure provides a simple and efficient way to produce large numbers of uniformly-shaped multicellular clusters 185 from each of which multicellular spheroid-like structures and multicellular spheroids can be formed for biomedical applications in tissue engineering, translational medicine, pharmaceutical industry and basic life science research.

Figure 9:
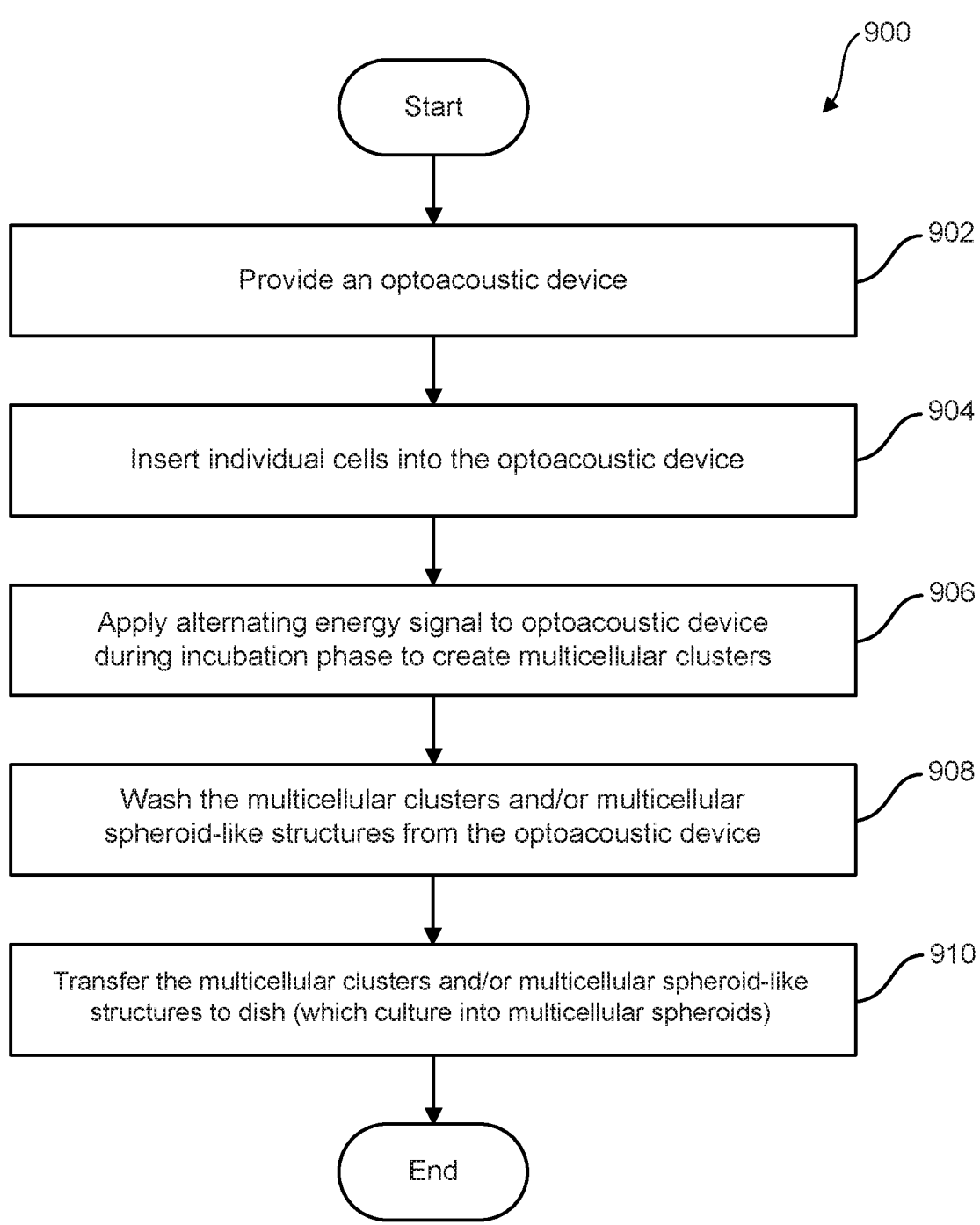
FIG. 9 is a method of creating multicellular cell clusters, spheroid-like structures and multicellular spheroids using an acoustofluidic device of the present disclosure.

Referring to FIG. 9, there is shown a method 900 of creating multicellular clusters, spheroid-like structures and multicellular spheroids 185 using the acoustofluidic device 100 of the present disclosure. Step 902 includes providing the acoustofluidic device 100 described hereinabove. For example, such device may include an acoustic interdigital transducer having a first end, a second end, a length between the first end and the second end, and a longitudinal axis parallel to the length. The interdigital transducer is configured to produce a plurality of SAWs substantially parallel to the length of the piezoelectric substrate 102 between the two electrodes 104, 106. The device also includes a chamber 108 having an array 122 of channels 124, wherein each of the channels 124 has a first end, a second end, a length between the first end and the second end. The channels 124 also have a longitudinal axis parallel to the length, and it is preferable that the chamber 108 is disposed over the interdigital transducer and oriented such that the longitudinal axis of the channels 124 is parallel with the longitudinal axis of the interdigital transducer.

Step 904 includes randomly inserting a plurality of individual cells 180 into the channels 124, wherein the channels 124 comprise a suspension fluid. That is, the individual cells 180 may be included in a suspension fluid, which is deposited into the array 122 of channels 124. A potentially advantageous way of depositing the individual cells 180 into the channels 124 may include forming a plurality of holes or reservoirs 110 that are fluidly coupled to recesses 127 at the ends of the channels 124, as shown in FIGS. 1E and 1F. For example, one recess may be greater than the width of one channel and be fluidly connected to that channel, a second recess may be greater than the size of the first recess and greater than the width of at least two channels and be fluidly connected to the at least two channels and the first recess, a third recess may be greater than the size of the second recess and greater than the width of at least three channels and be fluidly connected to the at least three channels and the first and second recesses. As such, a suspension fluid having a plurality of individual cells 180 disposed therein can be inserted directly into the reservoir 110 and conveyed to the larger recesses 127 at the ends of the channels 124, and the suspension fluid and cells 180 will disperse into the channels 124 as a result of the channels 124, recesses 127 and reservoirs 110 being in fluid communication with one another. This feature will also increase the throughput rate of fabricating multicellular clusters 185 and thus increase the rate of fabricating multicellular spheroid-like structures and multicellular spheroids.

Referring again to FIG. 9, immediately or soon after the individual cells 180 are disposed in the channels 124, the cells 180 will be in their incubation phase. As shown in step 906, during the incubation phase, an alternating signal is applied to the IDT at a frequency between 0.5 megahertz and 50 megahertz, thereby creating SAWs 134 within suspension liquid contained within the channels 124, wherein the SAWs 134 produce a plurality of pressure nodes 135 within the channels 124 and the SAWs 134 move the individual cells 180 toward the pressure nodes 135, thereby facilitating the formation of multicellular clusters 185 at the pressure nodes 135 in an array pattern within the channels 124. The alternating signal and SAW may consistently be applied for a period of between about 0 to 60 minutes including any increment or range therebetween, such as 1, 2, 3, 4, 5, 6, 7, 8, 9, 10, . . . , 20, . . . , 30, . . . , 40, . . . 50, . . . , 59 minutes. After the multicellular clusters 185 are formed, they are further cultured in the chamber 108 to form multicellular spheroid-like structures that are washed from the channels 124 in step 908 and transferred to a dish 160 for culturing in step 910. Optionally, multicellular clusters 185 are removed from the device prior to further culturing to form multicellular spheroid-like structures in a separate device, such as a dish 160. It is in step 910 that the multicellular spheroid-like structures formed from the multicellular clusters 185 transform to multicellular spheroids. Depending upon the type of cells, the culturing step 910 may continue for minutes, hours or days, such as 1-60 minutes, 1-24 hours or 1-7 days or any increment or range therebetween until culturing results in multicellular spheroids formation. Regardless, of the culturing time in the dish, this culturing time to create spheroids will be and/or will have been substantially reduced by first creating the multicellular cell clusters 185 in the acoustofluidic device 100 through the application of the SAW prior to transferring the individuals cells 180, multicellular cell clusters 185 and/or the multicellular spheroid-like structures to the dish 160.

The duration of culturing of the multicellular clusters 185 on the device to form multicellular spheroid-like structures also depends on the cell type, and may range from 30 minutes to about 10 hours, including any increment therebetween, such as 35 minutes, 40 minutes, 45 minutes, 50 minutes, 55 minutes, 1 hour, 1 hour and 5 minutes, 1 hour and 10 minutes, 1 hour and 15 minutes, 1 hour and 20 minutes, 1 hour and 25 minutes, 1 hour and 30 minutes, 1 hour and 35 minutes, 1 hour and 40 minutes, 1 hour and 45 minutes, 1 hour and 50 minutes, 1 hour and 55 minutes, 2 hours, 2 hours and 5 minutes, 2 hours and 10 minutes, 2 hours and 15 minutes, 2 hours and 20 minutes, 2 hours and 25 minutes, 2 hours and 30 minutes, 2 hours and 35 minutes, 2 hours and 40 minutes, 2 hours and 45 minutes, 3 hours and 50 minutes, 2 hours and 55 minutes, 3 hours, 3 hours and 5 minutes, 3 hours and 10 minutes, 3 hours and 15 minutes, 3 hours and 20 minutes, 3 hours and 25 minutes, 3 hours and 30 minutes, 3 hours and 35 minutes, 3 hours and 40 minutes, 3 hours and 45 minutes, 3 hours and 50 minutes, 3 hours and 55 minutes, 4 hours, 4 hours and 45 minutes, 4 hours and 10 minutes, 4 hours and 15 minutes, 4 hours and 20 minutes, 4 hours and 25 minutes, 4 hours and 30 minutes, 4 hours and 35 minutes, 4 hours and 40 minutes, 4 hours and 45 minutes, 4 hours and 50 minutes, 4 hours and 55 minutes, 5 hours, 5 hours and 5 minutes, 5 hours and 10 minutes, 5 hours and 15 minutes, 5 hours and 20 minutes, 5 hours and 25 minutes, 5 hours and 30 minutes, 5 hours and 35 minutes, 5 hours and 40 minutes, 5 hours and 45 minutes, 5 hours and 50 minutes, 5 hours and 55 minutes, 6 hours, 6 hours and 6 minutes, 6 hours and 10 minutes, 6 hours and 15 minutes, 6 hours and 20 minutes, 6 hours and 25 minutes, 6 hours and 30 minutes, 6 hours and 35 minutes, 6 hours and 40 minutes, 6 hours and 45 minutes, 6 hours and 50 minutes, 6 hours and 55 minutes, 7 hours, 7 hours and 5 minutes, 7 hours and 10 minutes, 7 hours and 15 minutes, 7 hours and 20 minutes, 7 hours and 25 minutes, 7 hours and 30 minutes, 7 hours and 35 minutes, 7 hours and 40 minutes, 7 hours and 45 minutes, 7 hours and 50 minutes, 7 hours and 55 minutes, 8 hours, 8 hours and 5 minutes, 8 hours and 10 minutes, 8 hours and 15 minutes, 8 hours and 20 minutes, 8 hours and 25 minutes, 8 hours and 30 minutes, 8 hours and 35 minutes, 8 hours and 40 minutes, 8 hours and 45 minutes, 8 hours and 50 minutes, 8 hours and 55 minutes, 9 hours, 9 hours and 9 minutes, 9 hours and 10 minutes, 9 hours and 15 minutes, 9 hours and 20 minutes, 9 hours and 25 minutes, 9 hours and 30 minutes, 9 hours and 35 minutes, 9 hours and 40 minutes, 9 hours and 45 minutes, 9 hours and 50 minutes, and 9 hours and 55 minutes.

The device can be used with any biological cell that is capable of 3D cell culture. Cells may be prokaryotic, such as bacteria, or eukaryotic, such as mammalian cells. Mammalian cells include rodent cells, carnivore cells, and primate cells. In some embodiments, cells are animal cells, such rodent cells or non-human primate cells. In some embodiments, cells are human cells. The cells can be the same or a mixture of different types of cells. In some embodiments, the cells are of animal and/or human origin and normal cells or diseased cells of animal and/or humanized animal and/or human origin. Examples include normal, infected, malignant, or otherwise diseased cells from various stages of disease progression. These cells may be primary cells, secondary cells, cell lines, transfected cells, transgenic cells, or stem cells, among others. A non-limiting list of exemplary cells includes cells from connective, nervous, muscle, epithelial, and/or vascular tissues. Exemplary cells are cells from brain, spinal cord, heart, liver, intestine, pancreas, gallbladder, kidney, lung, breast, ovary, thyroid, cartilage, muscle, skin, immune system cells, or stem cells.

Experiment and Experimental Results

Cell Preparation

Human breast cancer cell line MCF-7, human lung cancer cell line A549, human ovarian cancer cell line A2780, and murine embryonic carcinoma cell line P19 were purchased from the American Type Culture Collection (ATCC, Rockville, Md.). The murine pancreatic cancer cell lines Panc02 and UN-KC-614 were obtained from Dr. Surinder K. Batra (University of Nebraska). MCF-7 cells, A549 cells, Panc02 cells, and UN-KC-6141 cells were maintained in Dulbecco's modified Eagle medium (GIBCO), supplemented with 10% fetal bovine serum (FBS; GIBCO) and 100 U/mL penicillin/streptomycin (P/S; GIBCO). A2780 cells were maintained in RPMI-1640 medium (GIBCO), supplemented with 10% fetal bovine serum (FBS; GIBCO) and 100 U/mL penicillin/streptomycin (P/S; GIBCO). P19 cells were cultured in Alpha Modified Eagle's Medium (Corning, N.Y.) supplemented with 10% fetal bovine serum (FBS; Gibco) and 100 U/mL penicillin/streptomycin (P/S; Gibco). All cells were cultured in a humidified incubator supplemented with 5% $CO_2$ at 37° C. Cell suspensions were made by dissociating cells with 0.25% trypsin-EDTA (Gibco 25200, Invitrogen Co.), centrifuging dissociated cells at 400 g for 5 min at room temperature and re-suspending in culture media. Cell density was enumerated using a hemocytometer.

Device Fabrication

A microfluidic chamber for high-throughput fabrication of multicellular clusters, multicellular spheroid-like structures and multicellular spheroids was produced by soft lithography from Sylgard 184 polydimethylsiloxane (PDMS) using molds made with SU-8. After drilling holes for an inlet and outlet with a puncher (1 mm diameter, Harris Uni-Core, USA), oxygen plasma treatment was utilized (PDC001, Harrick Plasma, USA) to bind the molded PDMS chamber to a thin layer of PDMS film (25 micron (μm) thickness) that was spin coated on a surface polished silicon wafer.

An acoustic transducer, i.e., a standing surface acoustic wave (SSAW) generator was fabricated by a standard soft lithography and lift-off process. A 7-μm-thick photoresist layer (S1813, MicroChem, USA) was spin-coated on a piezoelectric substrate (a 500-μm-thick, double-side polished, 128° YX-propagation lithium niobate $LiNbO_3$ wafer). Then, the designed interdigital transducer (IDT) patterns of 40 electrode pairs with 75 μm finger width and periodic spacing were transferred from a plastic mask (Kunshan Kaisheng Electronics Co., Ltd, China) to the substrate by UV exposure. The IDT patterns were developed in a photoresist developer (MF CD-26, Microposit, USA) and deposited with double metal layers (Cr/50 Å, Au/600 Å) by a thermal evaporation (JSD-350, Anhui Jiaoshuo Vacuum Technology Co., Ltd, China). IDTs on the piezoelectric substrate were finally obtained after a standard lift-off process. Then the resonant frequency of the fabricated SSAW generator was measured at around 13.13-13.41 MHz using a network analyzer (E8362C, Agilent, USA).

Before cell assembly, the chamber was sterilized by autoclaving at 121° C. for 30 min. The acoustofluidic device can be assembled by coupling a disposable chamber with multiple cell assembly channels onto a reusable SSAW generator using a thin layer of oil. Mineral oil (SLBX1961, SIGMA, USA) was chosen as the coupling material to introduce the acoustic waves from the substrate to the device. In comparison with water or olive oil or other coupling materials, mineral oil may offer both a lower evaporation rate and a better coupling performance without causing harm to cell viability.

Figure 1G:
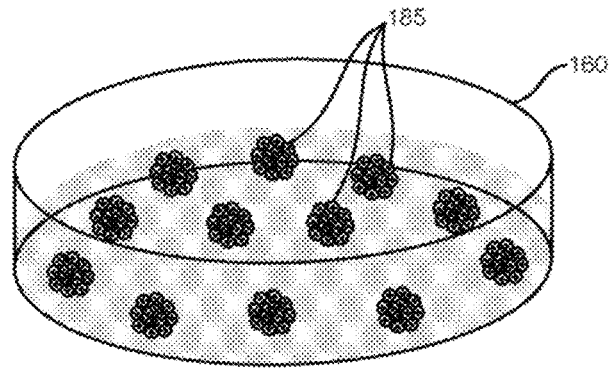
FIG. 1G illustrates a plurality of multicellular spheroid-like structures and/or cell spheroids in a dish.

The acoustofluidic device was fabricated by bonding a thick PDMS stamp with parallel spheroid assembly channels onto a thin PDMS layer (FIG. 1A). Once the radio frequency (RF) signal was applied, a SSAW field was generated by the SSAW generator, propagated on the piezoelectric substrate, and leaked into the PDMS channels through the thin layer of coupling oil between the SSAW generator and silicone layer. When the SSAW entered into the channels and met with the liquid culture medium containing suspended single cells, a linear pressure node distribution was formed inside of each channel. The suspended single cells were moved towards and trapped into the pressure node under the drive of acoustic radiation forces in each channel (FIG. 1D). With a 3 min acoustofluidic treatment, randomly distributed cells (FIG. 1E) were moved to the nearby pressure nodes and acoustically-assembled into 3D multicellular aggregates in a large-scale dot-array pattern (FIG. 1F). 12,000 pressure nodes were generated at the same time within one PDMS device, resulting in 12,000 cell aggregates. After incubation occurs using the acoustofluidic device to form 3D multicellular clusters (FIG. 1D, 185), these 3D cell aggregates are cultured such that cell-cell contacts are developed, and the multicellular clusters self-assemble into mature aggregates, such as spheroid-like structures, Spheroid-like structures possess sufficient cell-cell adhesion that they can be washed from the disposable chamber and cultured in ultra-low attachment dishes 160 (FIG. 1G), thus permitting the SSAW generator to be reused for another spheroid assembly experiment.

High-Throughput Acoustic Cell Assembly

In the cell patterning experiment, cells were aggregated into linear assembly arrays in PDMS channels by applying a radio frequency signal produced by a function generator (AFG3102C, Tektronix, USA) and modulated with an amplifier (25A100A, Amplifier Research, USA) to the IDT pair. The movement of cells was monitored and recorded by a microscope (IX-81, Olympus, Japan) with a CMOS camera (ORCA-Flash 4.0, HAMAMATSU, Japan) connected to a computer (Cellsens). The input voltages on the devices were from 10 to 60 Vpp (peak-to-peak voltage). Different kinds of cells were resuspended in type I collagen (Life Technologies, USA) and injected after the acoustic field was formed. The whole acoustic cell aggregation process took about one minute. Generally, cells are exposed to the acoustic field for a sufficient amount of time such that cells are moved to pressure nodes and thereby form 3D cell clusters or aggregates ("multicellular clusters"). Multicellular clusters mean a plurality of individual cells contacting one another with zero to minimal cell-to-cell adhesion. The amount of time for the acoustic field exposure to the cells is from several seconds up to several minutes, and may be independent of the cell type. After exposure to the acoustic field, the multicellular clusters may be incubated in the PDMS device for a sufficient amount of time to form mature aggregates ("spheroid-like structures"). Alternatively, the multicellular clusters may be transferred to another container, such as an ultra-low attachment plate, to form spheroid-like structures. Spheroid-like structures form from cell clusters by development of additional cell-to cell adhesion. Generally, spheroid-like structures have cell-to-cell adhesion sufficient to permit further manipulation, such as removal from the PDMS device to a petri-dish, without substantial or any disruption of the mature aggregates. However, as discussed elsewhere herein, cell-to-cell adhesion varies depending on the cell type, and use of the device is not limited to cell types forming mature aggregates having extensive cell-cell adhesion. Spheroid-like structures can then be further incubated for additional cellular proliferation and formation of spheroids, such as those depicted in FIGS. 5 and 6. In this example, to form cell spheroids, the cell clusters formed by the acoustic field were incubated in the PDMS device for a short period and subsequently transferred into ultra-low attachment plates (Corning, USA) with fresh cell culture medium for incubation. The cell cluster plates were incubated and maintained at 5% $CO_2$ and 37° C. These cell clusters were imaged and recorded every day for several days during which spheroid-like structures and multicellular spheroids formed.

Figures 2A, 2B:
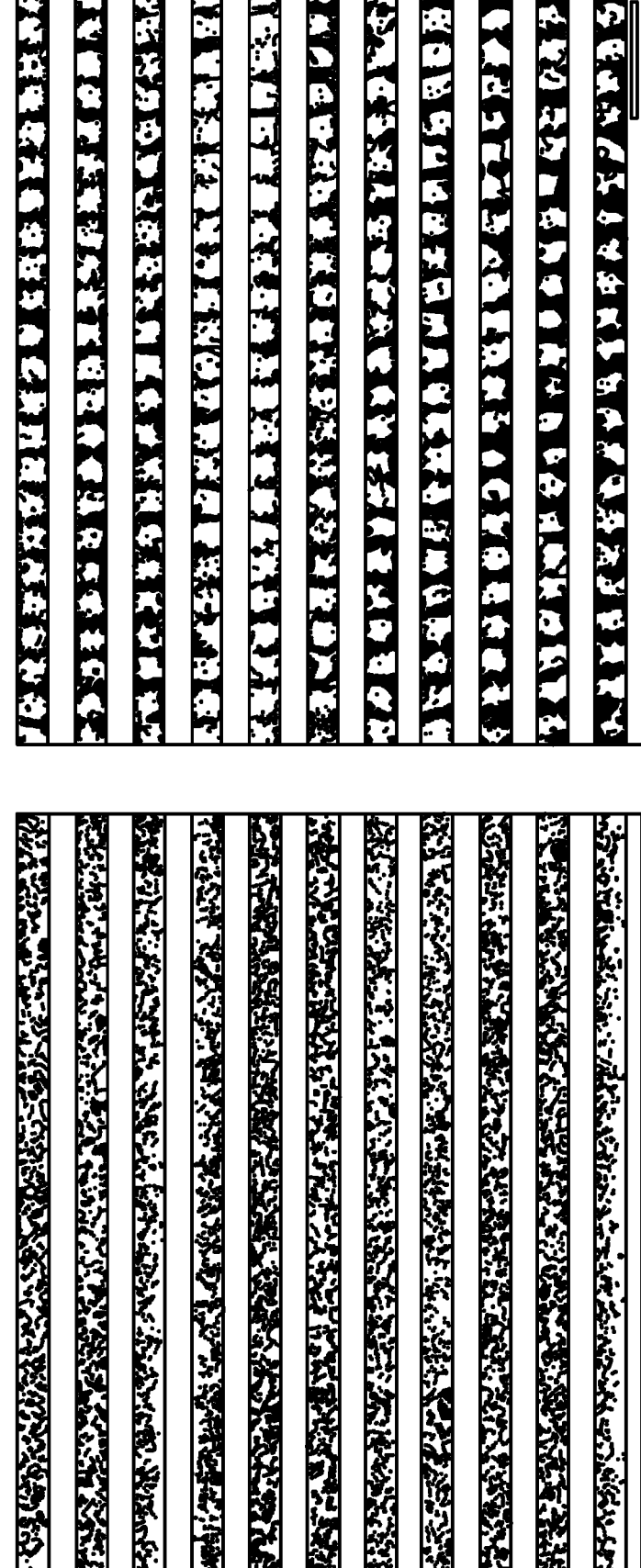
FIG. 2A is a black and white replica of a photograph of a plurality of individual cells randomly disposed within a plurality of channels when the acoustofluidic device is in the OFF position.
FIG. 2B is a black and white replica of a photograph of a plurality of multicellular clusters and/or multicellular spheroid-like structures arranged consistently as an array within each of the channels, wherein the array is consistent with the nodes of the acoustic surface waves formed when the acoustofluidic device is in the ON position.
Figure 2C:
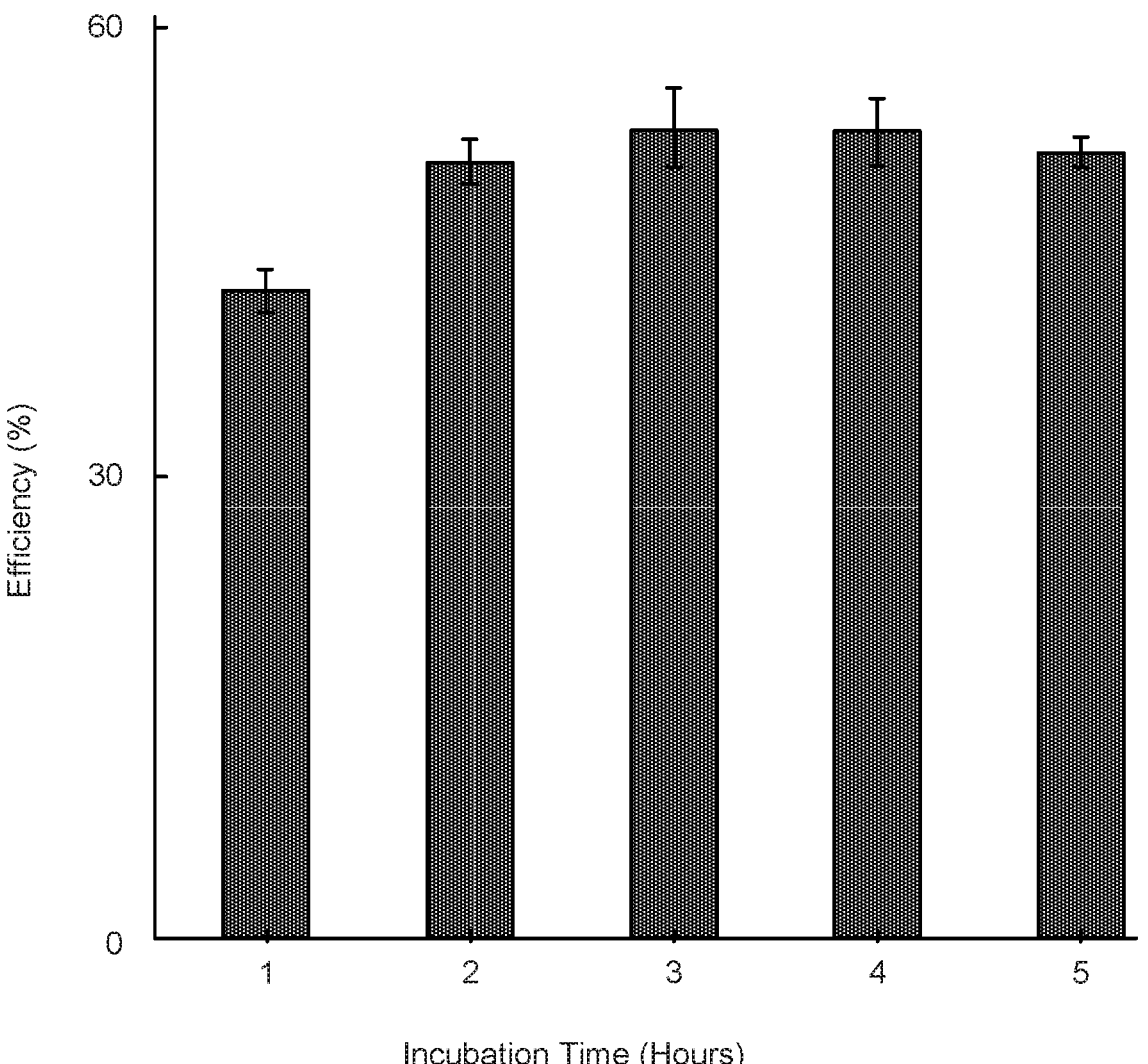
FIG. 2C is a bar graph illustrating the efficiency of multicellular spheroid-like clusters as a function of incubation time that the individual cells are within the channels after the acoustofluidic device is in the ON position.
Figure 2D:
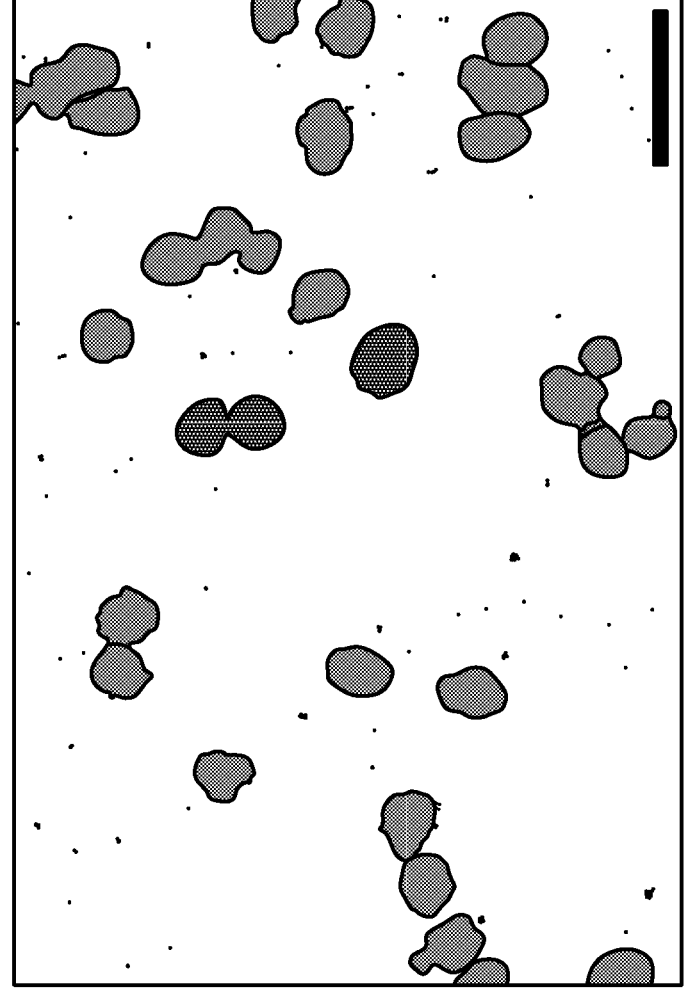
FIG. 2D is a black and white replica of a photograph of Panc02 cell spheroid cultures in an ultra-low attachment petri-dish after one day of culture.

Referring to FIG. 2A, there is shown a microscopic image of a large scale acoustofluidic assembly of cells. After applying the acoustic field for minutes, the Panc02 cells were trapped into 3D cell aggregates in a large-scale, dot-array format, as shown in FIG. 2B. To maintain the multicellular cell aggregates during transfer from the PDMS device into the ultra-low attachment petri-dish, on-chip incubation time was optimized to from about 1 to about 5 hours to form spheroid-like structures. If the incubation time was more than 2 hours for cell-cell adhesion, Panc02 spheroids remained largely intact after the transfer process, at an efficiency of approximately 50% (50.54±1.43% to 52.75±2.58%) (FIG. 2D). For this experiment, 2 hours was determined as the optimal incubation time for cell aggregates to form cell-cell contacts. See FIG. 2C. The skilled artisan is readily able to determine the optimal incubation time for other cell types to form spheroid-like structures. The transfer of the acoustic assembled spheroid-like structures from the device to an ultra-low attachment petri-dish yielded more than 6,000 cell spheroids after one day culture (FIG. 2D—(Scale bar: 500 micrometers)) and provided a much better production throughput with shorter formation time than other methods, as shown in Table 1 in FIG. 8.

Spheroid Formation and Culture Compared with Commercial Technology To compare the results using the acoustofluidic device of the disclosure with Corning spheroid microplates, Panc02 cells were harvested as single cell suspension with 0.25% Trypsin-EDTA solution (Gibco 25200, Invitrogen Co.) for 2 min at 37° C., centrifuged at 400 g for 5 min and resuspended in the respective culture media for the acoustofluidic device or for the microplates. The harvested cells were seeded at fixed density of 500 cells per well into Corning® spheroid microplates (Corning, USA), spun down at 400 g for 3 min and incubated at 37° C., 5% $CO_2$. Spheroid cultures were visualized at 0-7 days using a microscope and compared side-by-side with the disclosed acoustic assembly method.

Figure 3:
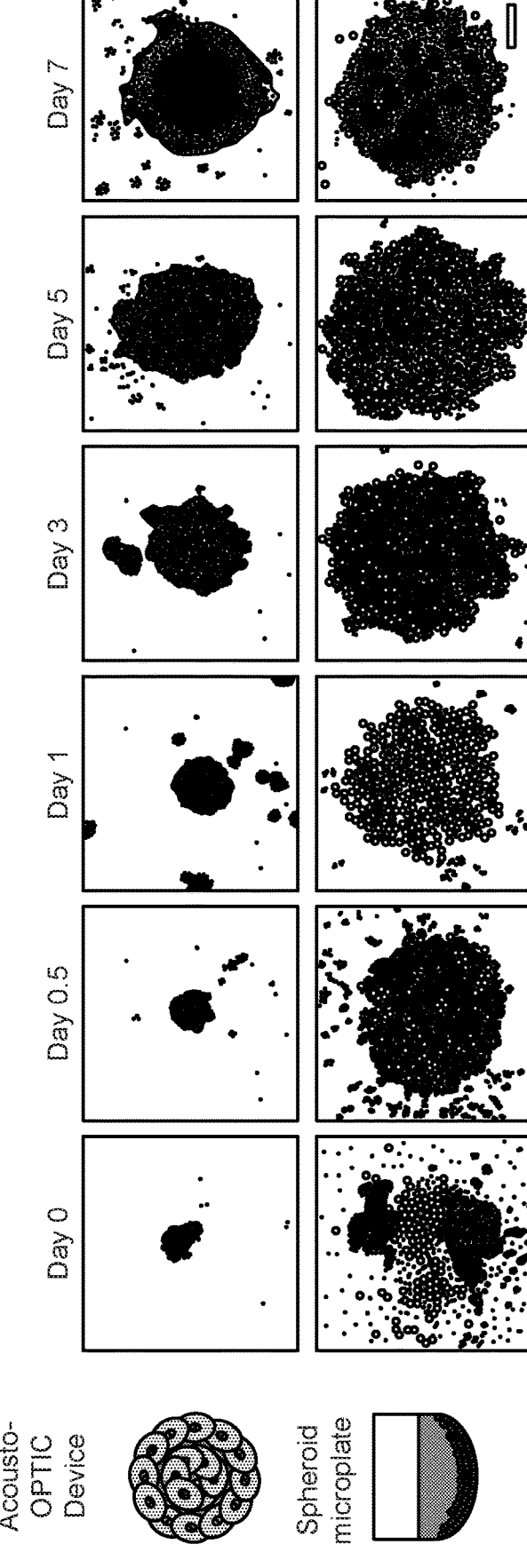
FIG. 3 depicts two rows of black and white replicas of photographs of the development of multicellular clusters developing into multicellular spheroid-like structures and multicellular spheroids formed in an acoustofluidic device (top row) in comparison to the development of the same cells in multicellular spheroid-like structures and spheroids in a Corning® spheroid microplate (bottom row) during the same duration.

Tumor spheroid cultures were visualized at day 0, day 0.5, day 1, day 3, day 5, and day 7. As shown in FIG. 3, Panc02 cells in the multicellular clusters started to form spheroid-like structures at 12 hours (Day 0.5) using the inventive acoustic assembly approach, whereas spheroid-like structures were not formed until day 3 using commercial microplates. Thus, the disclosed acoustic assembly platform accelerated spheroid formation.

Validation of Acoustic Assembled Tumor Spheroid
Proliferation and Viability

The proliferation of acoustically assembled cell spheroids was assessed using a cell counting kit-8 (CCK-8; Sigma-Aldrich, St. Louis, Mo., USA) according to the manufacturer's instructions. Control cells were exposed to an equivalent amount of vehicle. Tumor spheroids or cultured tumor cells were incubated in the CCK-8 solution for 4 h, and the supernatants were transferred to 96-well plates. Cell proliferation was assessed by measuring the absorbance at 450 nm using the Epoch™ microplate spectrophotometer (Bio-Tek Instruments, USA). The viability testing was achieved by the live/dead stain assay (live/dead viability kit, L3224, Thermo Fisher Scientific Inc.). Tumor spheroids were stained with a mixture of 2 micromolar (µM) Calcein AM and 4 µM ethidium homodimer-1 to stain for live and dead cells, respectively. Brightfield and fluorescent images were captured using a microscope (IX83, Olympus, Japan).

Tumor Spheroid Characterization

Figure 4A:
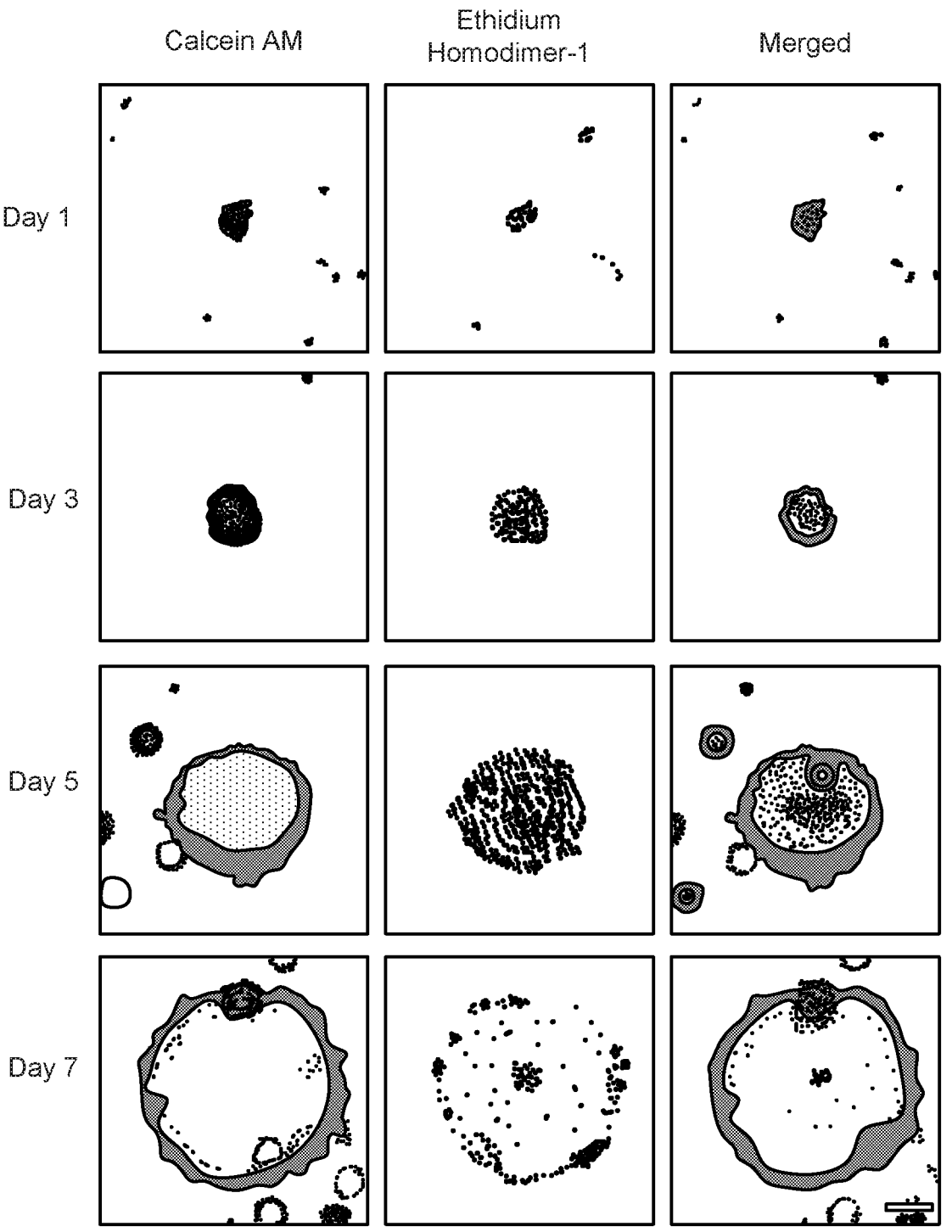
FIG. 4A depict live/dead stained Panc02 multicellular clusters, multicellular spheroid-like structures and multicellular spheroids cultured in an ultra-low attachment dish for one week. Cells were stained with Calcein AM (left column) or eithidium homodimer (center column) for live/dead detection. The right column depicts merged images of the Calceim AM and eithidim homodimer stained multicellular clusters, spheroid-like structures, and spheroids.
Figures 4B, 4C, 4D:
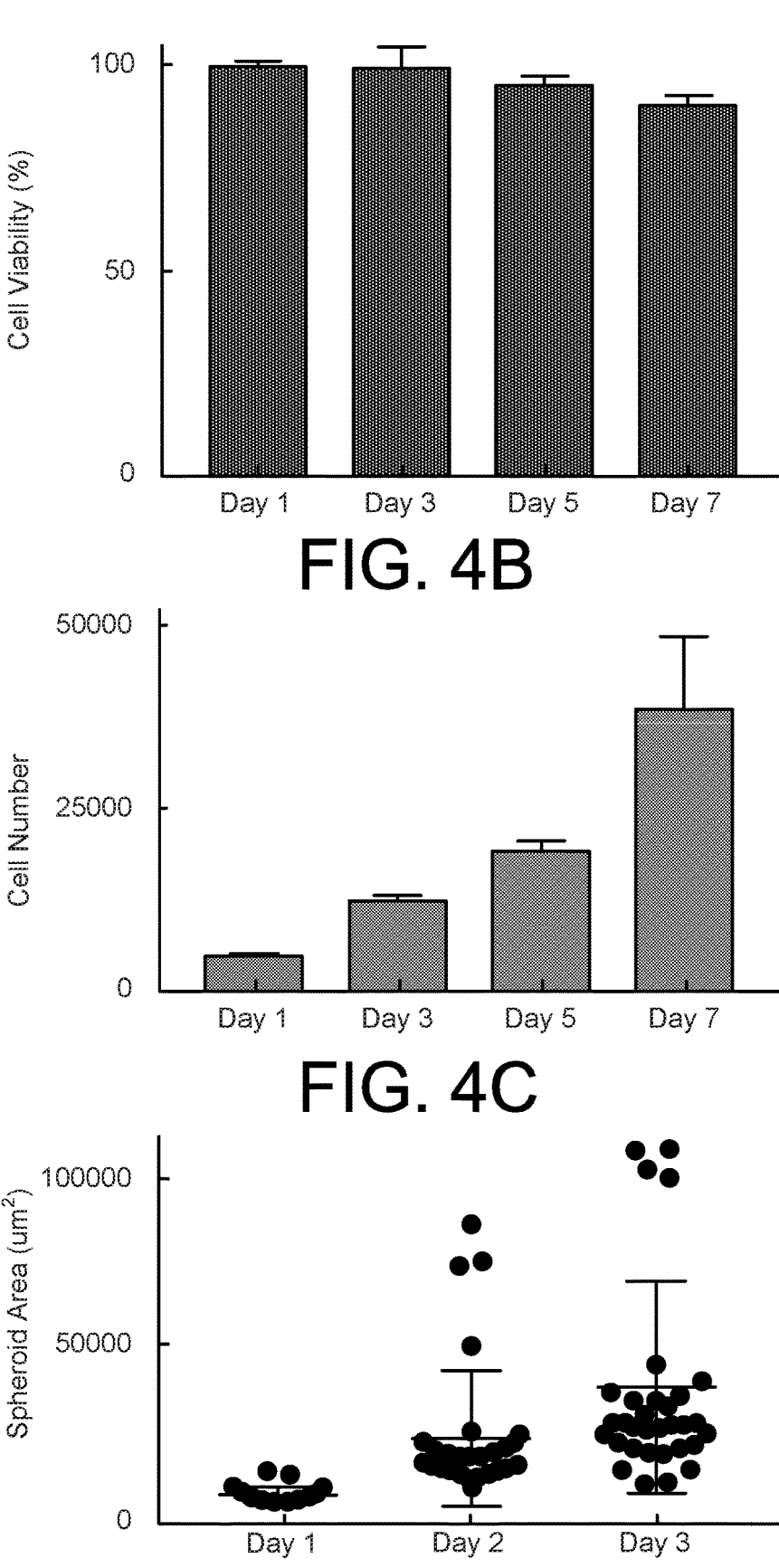
FIG. 4B is a bar graph illustrating the viability of Panc02 cells in multicellular spheroid-like structures and multicellular spheroids.
FIG. 4C is a bar graph illustrating the cell number (as a measure of proliferation) of Panc02 cells in multicellular spheroid-like structures and multicellular spheroids.
FIG. 4D is a graph illustrating the sizes of Panc02 multicellular clusters, spheroid-like structures, and multicellular spheroids.

To characterize the developed cell spheroids, mouse pancreatic cancer cell line-Panc02 cells were acoustically-assembled into multicellular clusters as described above and cultured for 7 days. Cell viability and proliferation rates were characterized using live/dead staining and cell counting kit-8 tests. FIG. 4A and FIG. 4B show the live/dead staining of Panc02 cell spheroids over a 7-day culture, indicating that the majority of cells (>90%) remained viable after 7 days of culture. Cell proliferation was assessed using the cell counting kit-8. The number of cells within the Panc02 spheroids increased dramatically during the 7-day culture indicating a healthy proliferation in the dish (FIG. 4C). In addition, the size uniformity of the Panc02 cell spheroids was characterized from Day 1 to Day 3. FIG. 4D shows the size distribution of cell spheroids. As seen, the cell spheroids formed by the herein disclosed method had good uniformity initially, and size difference increases as spheroids start to merge occasionally during the boundary and matrix free culture (FIG. 2D).

Figure 5:
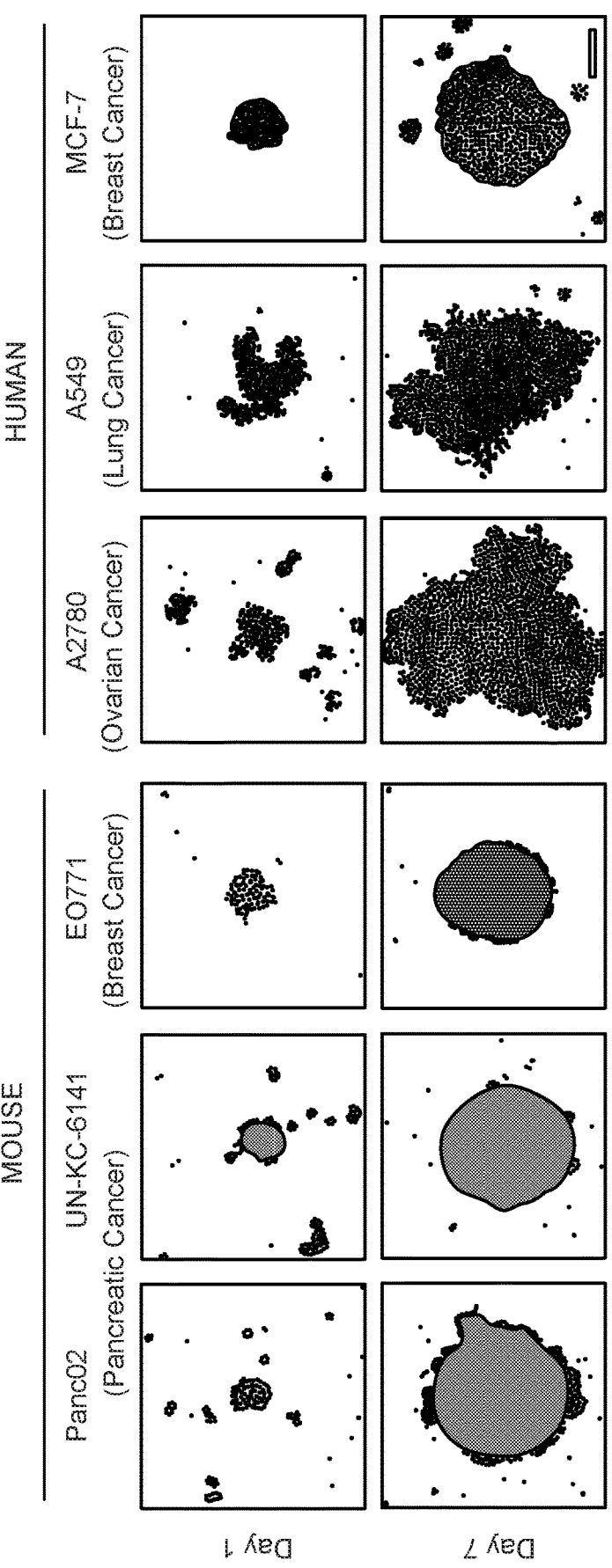
FIG. 5 depicts black and white replicas of photographs of multicellular clusters and/or spheroid-like structures (Day 1) and/or multicellular spheroids (Day 7), formed from different cell types using the acoustofluidic device.

Six different types of mouse and human cancer cell lines were tested. As shown in FIG. 5, murine pancreatic cancer cell lines Panc02 and UN-KC-6141, murine breast cancer cell line EO771 and human breast cancer cell line MCF-7 cell spheroids showed smooth boundary and compact spheroidal shape after 7 days of culture, whereas human ovarian carcinoma cell line A2780, and human lung cancer cell line A549 formed only loose aggregates after 7 days of culture. The aggregates of human cancer cell lines can be easily disrupted mechanically by pipetting, suggesting the cell-cell contacts established by these cultures are weak. This difference between mouse and human cancer cell line spheroids is consistent with other reports using scaffold free spheroid formation methods. This observed spheroid morphology did not change in cultures maintained up to 14 days. This suggests that the disclosed acoustic cell assembly system produces both for both human and murine spheroids with characteristics consistent with lower throughput methodologies.

Tumor Spheroids Hypoxia Characterization

To examine the formation of hypoxia core, tumor spheroids were stained with Image-IT™ Hypoxia Reagent (Invitrogen™, USA) according to the manufacturer's instruction. The reagent was added to the spheroids at a final concentration of 10 µM and incubated at 37° C. for 48 hours. The spheroids were then imaged on the fluorescence microscope with excitation/emission of 490/610 nm. As shown in FIGS. 6A-6D, spheroids of mouse embryonic cell line P19, and mouse pancreatic cancer cell lines Panc02 and UN-KC-6141 were cultured for 10 days to allow for formation of the hypoxic core. As indicated by the staining, hypoxic cores were present in the center of the spheroid. The hypoxic centers of the spheroids were similar to those reported for other assembly methods.

Figures 6A, 6B, 6C, 6D:
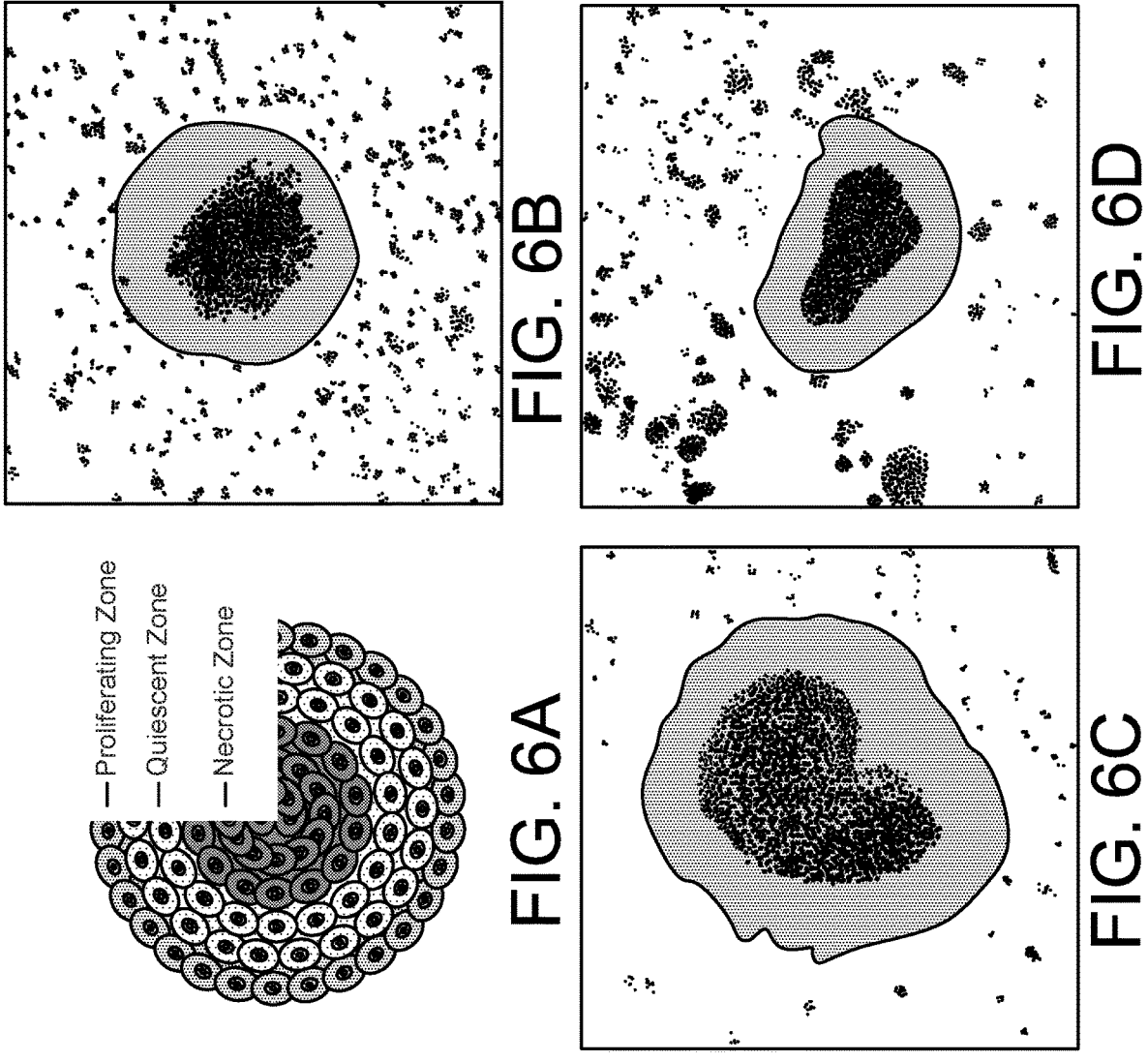
FIG. 6A illustrates a hypoxic core of a tumor spheroid.
FIGS. 6B-6D depict black and white replicas of photographs of multicellular spheroids formed from different cell types.

FIGS. 6A-6D illustrate the hypoxic core of various tumor spheroids. FIG. 6A shows the three-layered structure of the tumor spheroids including proliferating zone, quiescent zone, and necrotic zone (from outside to inside). The hypoxic region encompasses the necrotic zone and may also include some of the quiesent zone. FIG. 6B shows the hypoxic regions (the darker area in the center) of a P19 cell spheroid. FIG. 6C shows the hypoxic regions of a Panc02 cell spheroid and FIG. 6D shows the hypoxic regions of a UN-KC-6141 cell spheroid (scale bar: 200 µm).

Cytotoxicity Assay

The cytotoxic effect of the chemotherapeutic drug Gemcitabine (LC Laboratories, Woburn, Mass., USA) on Panc02 cell spheroids culture was compared to the cytotoxic effect on monolayer culture. For the cytotoxic assay, $1 \times 10^4$ cells suspended in complete medium were seeded in each well of a 96-well plate. Four (4)-day-old Panc02 spheroids were transferred to a new 96 ultra-low attachment well plate. The next day, the cells and spheroids were treated with different concentrations of Gemcitabine solution (0, 0.1, 1, 10, 25, 50, 100 µM) in sextuplicate wells. After incubating the cells with Gemcitabine for 48 h, 20 microliter (µl) of 3-(4,5-dimethylthiazol-2-yl)-2,5-diphenyltetrazolium bromide (MTT) solution (5 mg/ml) was added into each well, and the cells were incubated for 4 hours. While the monolayer culture was left untouched in the original plate, the content of each well containing the tumor spheroids culture was transferred to a new, flat bottom 96-well plate before the plate was centrifuged at 200×g for 5 minutes. Then, 100 µl of media was aspirated from each well from the plates containing the monolayer and spheroids cultures. The plates were then blotted dry on paper towels, followed by the addition of 100 µl of DMSO. Finally, absorbance was recorded at 570 nm using the Epoch™ microplate spectrophotometer (Bio-Tek Instruments, USA). The assay was carried out with 3 replicates for each culture.

Figure 7:
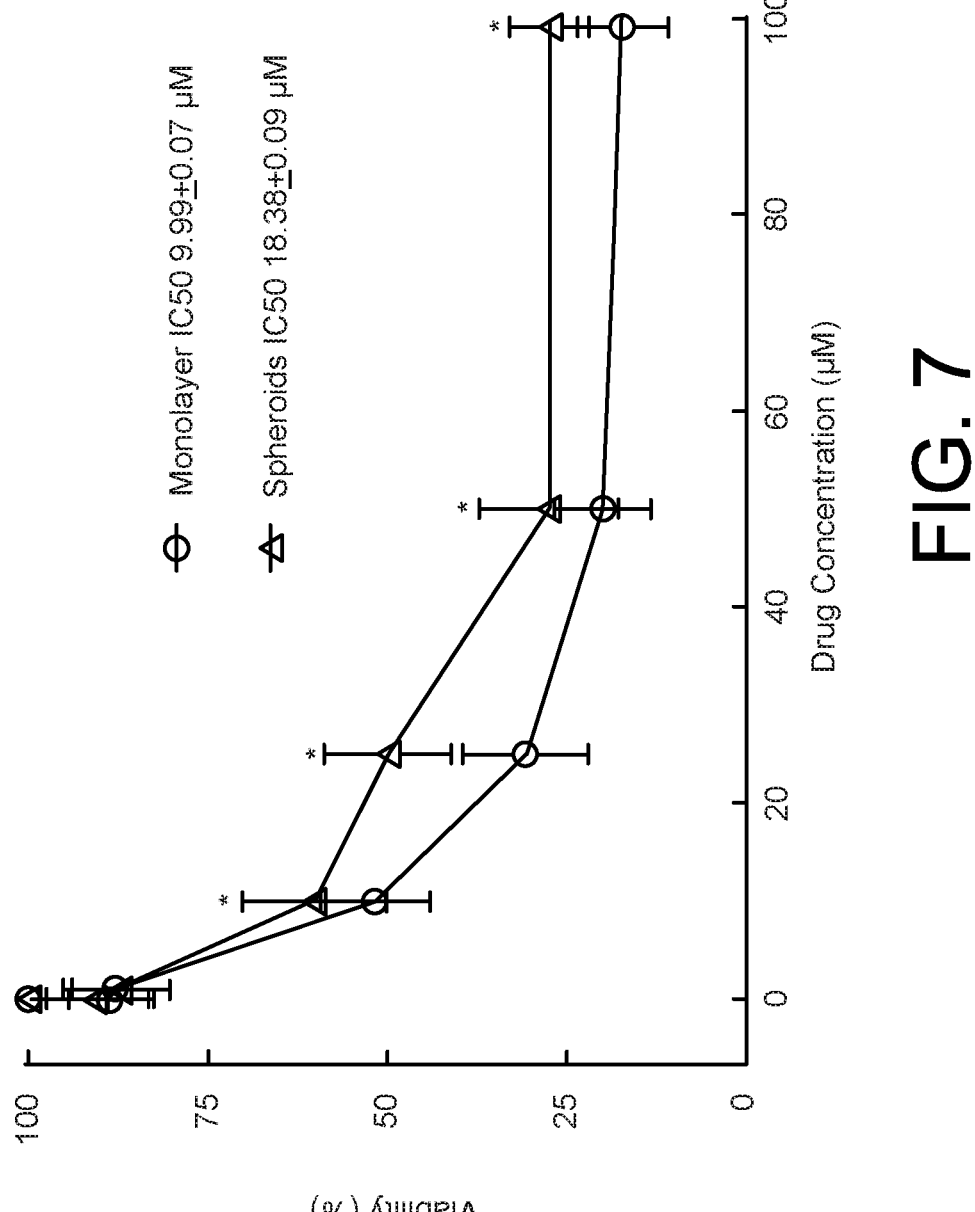
FIG. 7 illustrates a comparison of drug resistance, measured as viability as a function of drug concentration, of monolayer cultures compared to 3D spheroids formed using the acoustofluidic device.

Parallel experiments were set with traditional 2D monolayer cell cultures to examine differential response of 2D and 3D cell cultures. Cell number and viability were measured using MTT assay after 2 days of Gemcitabine treatment. The IC50 value was calculated. For the monolayer culture, the IC50 of Gemcitabine on Panc02 cells was 9.99±0.07 µM while the IC50 value for spheroids was 18.38±0.09 µM (FIG. 7). From the regression curves, both spheroids and monolayer cultures showed a dose-dependent response to the drugs. This indicated that Panc02 cells grown in the form of spheroids retained dosage-dependent cytotoxicity of the drug. However, spheroids were shown to confer a higher resistance to Gemcitabine treatment in comparison to its monolayer counterpart, which could be attributed to several characteristics of 3D culture.

FIG. 7 shows the drug (gemcitabine) resistance comparison between the monolayer cultures (circles) and spheroid models (triangles) using MTT assays. Monolayer and spheroidal cultures of Panc02 cells were exposed to gemcitabine for 2 days. The results are presented as means±S.E.M of three independent experiments. (*P<0.001).

Statistical Analysis

Data presented are representative of at least three independent experiments. All values are expressed as arithmetic mean±standard deviation (SD). Statistical difference between experimental groups was determined using Student's t test, when P values<0.05 were considered statistically significant.

Various modifications and additions can be made to the embodiments disclosed herein without departing from the scope of the disclosure. For example, while the embodiments described above refer to particular features, the scope of this disclosure also includes embodiments having different combinations of features and embodiments that do not include all of the described features. Thus, the scope of the present disclosure is intended to embrace all such alternatives, modifications, and variations as fall within the scope of the claims, together with all equivalents.

All publications, patents and patent applications referenced herein are hereby incorporated by reference in their entirety for all purposes as if each such publication, patent or patent application had been individually indicated to be incorporated by reference.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, for example, as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A device for fabricating multicellular spheroids from individual cells, the device comprising:
an interdigital transducer having a first end, a second end, a length between the first end and the second end, and a longitudinal axis parallel to the length, wherein the interdigital transducer is configured to produce a plurality of surface waves substantially parallel to the length;
a substrate having an array of channels, wherein each of the channels has a first end, a second end, a length between the first end and the second end, and a longitudinal axis parallel to the length, wherein the substrate is disposed over the interdigital transducer and oriented such that the longitudinal axis of the channels is parallel with the longitudinal axis of the interdigital transducer; and
a signal generator coupled to the interdigital transducer, wherein the generator produces an alternating signal to the interdigital transducer at a frequency between 0.5 megahertz and 50 megahertz and the interdigital transducer creates surface waves within suspension liquid contained within the channels, wherein the suspension liquid comprises a plurality of individual cells, and wherein the surface waves produce a plurality of pressure nodes within the channels and the surface waves move the individual cells toward the pressure nodes, thereby facilitating the formation of multicellular clusters at the pressure nodes;
wherein the substrate further comprises a first plurality of recesses disposed at the first end of the channels and a second plurality of recesses disposed at the second end of the channels, wherein one of the first plurality of recesses is greater in size than another of the first plurality of recesses, wherein the one of the first plurality of recesses is farther from the first end of the channel and is in fluid communication with the other of the first plurality of recesses.

2. The device of claim 1, further comprising a fluid layer disposed between the array and the interdigital transducer.

3. The device of claim 2, wherein the fluid layer comprises mineral oil.

4. The device of claim 1, further comprising a means for coupling the substrate to the interdigital transducer.

5. The device of claim 4, wherein the means for coupling the substrate to the interdigital transducer comprises one of (a) a plurality of pegs extending from the substrate and a corresponding plurality of holes in a chamber of the interdigital transducer or (b) a plurality of pegs extending from the chamber and a corresponding plurality of holes in the substrate.

6. The device of claim 1, wherein one of the second plurality of recesses is greater in size than another of the second plurality of recesses, wherein the one of the second plurality of recesses is farther from the second end of the channel and is in fluid communication with the other of the second plurality of recesses.

7. A device for fabricating multicellular spheroids from individual cells, the device comprising:
a means for producing a plurality of parallel surface acoustic waves, wherein the surface acoustic waves comprise a frequency between 0.5 megahertz and 50 megahertz;
a substrate having an array of channels, wherein each of the channels has a first end, a second end, a length between the first end and the second end, and a longitudinal axis parallel to the length, wherein the substrate is disposed over the means for producing a plurality of parallel surface acoustic waves and oriented such that the longitudinal axis of the channels is parallel with parallel surface acoustic waves; and
wherein the surface acoustic waves produce a plurality of pressure nodes within the channels and the surface acoustic waves move the individual cells toward the pressure nodes, thereby facilitating the formation of multicellular clusters in an array pattern within the channels;

wherein the substrate further comprises a first plurality of recesses disposed at the first end of the channels and a second plurality of recesses disposed at the second end of the channels, wherein one of the first plurality of recesses is greater in size than another of the first plurality of recesses, wherein the one of the first plurality of recesses is farther from the first end of the channel and is in fluid communication with the other of the first plurality of recesses.

* * * * *